United States Patent [19]
Liu et al.

[11] Patent Number: 5,976,563
[45] Date of Patent: *Nov. 2, 1999

[54] PESTICIDAL COMPOSITION AND *BACILLUS THURINGIENSIS* STRAIN

[75] Inventors: Chi-Li Liu, Davis, Calif.; Anita M. MacMullan, Davidson, N.C.; Patricia Ann Lufburrow, Davis, Calif.; Robert L. Starnes, Sacramento, Calif.; Denise C. Manker, Davis, Calif.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/946,895

[22] Filed: Oct. 8, 1997

Related U.S. Application Data

[63] Continuation of application No. 08/444,634, May 19, 1995, abandoned, which is a continuation-in-part of application No. 08/404,076, Mar. 14, 1995, abandoned, which is a continuation-in-part of application No. 08/212,462, Mar. 14, 1994, abandoned.

[51] Int. Cl.⁶ .................................................. A01N 25/02
[52] U.S. Cl. .................... 424/405; 424/93.461; 435/122; 514/255
[58] Field of Search ........................... 435/122; 514/255; 424/93.467, 405, 114, 115

[56] References Cited

U.S. PATENT DOCUMENTS

| | | |
|---|---|---|
| 3,944,664 | 3/1976 | Kitagaki et al. . |
| 4,016,265 | 4/1977 | Inoue et al. . |
| 4,206,281 | 6/1980 | Goldberg ................................. 435/30 |
| 4,764,372 | 8/1988 | Herrnstadt et al. ...................... 435/832 |
| 4,766,203 | 8/1988 | Krieg ................................. 424/93.461 |
| 4,910,016 | 3/1990 | Gaertner et al. . |
| 4,915,943 | 4/1990 | Gago et al. . |
| 5,024,837 | 6/1991 | Donovan et al. . |
| 5,204,100 | 4/1993 | Carozzi et al. .......................... 424/936 |
| 5,369,027 | 11/1994 | Lambert et al. ...................... 435/252.2 |
| 5,484,587 | 1/1996 | Branly et al. . |

FOREIGN PATENT DOCUMENTS

| | | |
|---|---|---|
| WO 90/13651 | 11/1990 | WIPO . |
| 9409630 | 5/1994 | WIPO . |
| WO 94/09630 | 5/1994 | WIPO . |
| 9525181 | 9/1995 | WIPO . |

OTHER PUBLICATIONS

Liu, *Chemical Abstracts*, vol. 121, 1993, #224298.
Stonard et al., In Natural and Engineered Pest Management Agents, Paul A. Mann, Robert M. Hollingworth, eds., ACS, Washington, D.C. pp. 25–36 (1994).
Yunlong et al., Acta Microbiologica Sinica vol. 33, No. 1, pp. 62–68.
Argauer et al., J. Entomol. Sci. vol. 26, No. 2, pp. 205–213 (1991).
Tailor et al., Molecular Microbiology, vol. 6, No. 9, pp. 1211–1217 (1992).

(List continued on next page.)

*Primary Examiner*—Neil S. Levy
*Attorney, Agent, or Firm*—Michael J. Ward; Dugal S. Sickert

[57] ABSTRACT

The invention is related to a novel strain(s) of *Bacillus thuringiensis* in which essentially all of the pesticidal activity of said strain is in the supernatant of a fermentation of said strain. The strain produces a substance which has activity against an insect pest(s) of the order Coleoptera and which enhances the pesticidal activity of a Bacillus related pesticide. The invention further relates to pesticidal compositions comprising the substance and a pesticidal carrier, or the substance and a Bacillus related pesticide, a chemical pesticide and/or a virus with pesticidal properties as well as methods of using the pesticidal compositions to control a pest.

3 Claims, 2 Drawing Sheets

OTHER PUBLICATIONS

Höfte et al., Microbiological Reviews, vol. 53, No. 2, pp. 242–255 (1989).

Levinson et al., J. Bacteriology, vol. 172, pp. 3172–3179 (1990).

Prystaš et al., Collection Czechoslov. Chem. Commun., vol. 40, pp. 1775–1785.

Luthy, FEMS Microbiology Letters, vol. 8, No. 1, pp. 1–7 (1980).

Feitelson et al., Bio/Technology, vol. 10, pp. 271–275 (1992).

"Entomocidal toxins of *bacillus thuringiensis*", *Pharmacology & Therapeutics*, Sep. 11, 1981.

Bene, G., "Action of *Bacillus thuringiensis* Preparation Against . . . ", *Experimentia*, 31(11):1288–1290 (1975).

Argauer, R.J., et al., "Produced by the HD 116 Strain of *Bacillus thuringiensis* var. *morrisoni*", *EPO–Biotech*, 26(2):205–213 (1991).

Asano, S., et al., "Enhancing Effects of Supernatants from Various Cultures of *Bacillus thuringiensis* on Larvicidal Activity of δ–Endotoxin against the Common Cutwork, *Spodoptera litura*", *Appl. Entomol. Zool.*, 30(2):369–374 (1995).

Asano, S., et al., "A Unique Insecticidal Activity in *Bacillus thuringiensis* Growth Medium", *App. Entomol. Zool.*, 29(1):39–45 (1994).

Burges, H.D., "Control of Insects by *Bacillus thuringiensis*", *Proc. 5th Br. Insectic. Fungic. Conf.*, vol. 2, 405–411 (1969).

Krieg, A., "Concerning α–Exotoxin Produced by Vegetative Cells of *Bacillus thuringiensis* and *Bacillus cereus*", *Journ. of Invert. Pathology*, 17:134–135 (1974).

Vankova, J., et al., "The Control of *Monomorium pharaonis* (hymenoptera: Formicidae) with *Bacillus thuringiensis*", *Journ. of Invert. Pathology*, 26:159–163 (1975).

Yendol, W.G., "Susceptibility of the Face Fly to Commercial Preparation of *Bacillus thuringiensis*", *Journ. of Economic Entomology*, 60(3):860–864 (1967).

PESTICIDAL COMPOSITION AND *BACILLUS THURINGIENSIS* STRAIN

This application is a continuation of U.S. patent application Ser. No. 08/444,634 now abandoned, filed May 19, 1995, which is a continuation-in-part of application Ser. No. 08/404,076, filed Mar. 14, 1995, now abandoned, which is a continuation-in-part of application Ser. No. 08/212,462, filed Mar. 14, 1994, now abandoned, and are hereby incorporated fully by reference.

FIELD OF THE INVENTION

The invention is related to a novel strain(s) of *Bacillus thuringiensis* in which essentially all of the pesticidal activity of said strain is in the supernatant of a fermentation of said strain. The strain produces a substance which has activity against an insect pest(s) of the order Coleoptera and which enhances the pesticidal activity of a Bacillus related pesticide. The invention further relates to pesticidal compositions comprising the substance and a pesticidal carrier, or the substance and a Bacillus related pesticide, a chemical pesticide and/or a virus with pesticidal properties as well as methods of using the pesticidal compositions to control a pest.

BACKGROUND OF THE INVENTION

Every year, significant portions of the world's commercially important agricultural crops, including foods, textiles, and various domestic plants are lost to pest infestation, resulting in losses in the millions of dollars. Various strategies have been used in attempting to control such pests.

One strategy is the use of broad spectrum pesticides, i.e., chemical pesticides with a broad range of activity. However, there are a number of disadvantages to using such chemical pesticides. Specifically, because of their broad spectrum of activity, these pesticides may destroy non-target organisms such as beneficial insects and parasites of destructive pests. Additionally, these chemical pesticides are frequently toxic to animals and humans, and targeted pests frequently develop resistance when repeatedly exposed to such substances.

Another strategy has involved the use of biopesticides, which make use of naturally occurring pathogens to control insect, fungal and weed infestations of crops. Biopesticides comprise a bacterium which produces a toxin, a substance toxic to the pest. Biopesticides are generally less harmful to non-target organisms and the environment as a whole than chemical pesticides.

The most widely used biopesticide is *Bacillus thuringiensis* (B.t.). B.t. is a widely distributed, rod shaped, aerobic and spore-forming microorganism. During its sporulation cycle, B.t. produces a protein(s) known as a crystal delta-endotoxin(s), which kills insect larvae. B.t., therefore, is very useful as an agricultural pesticide.

Some strains, e.g., *Bacillus thuringiensis* subsp. *kurstaki* and *Bacillus thuringiensis* subsp. *aizawai*, have been found to be specific for Lepidoptera. *Bacillus thuringiensis* subsp. *israelensis* has been found to be specific for Diptera (Goldberg, U.S. Pat. No. 4,166,112). Other strains, e.g., *Bacillus thuringiensis* subsp. *tenebrionis* (Krieg et al., 1988, U.S. Pat. No. 4,766,203), have been found to be specific for Coleoptera. The isolation of another coleopteran toxic *Bacillus thuringiensis* strain was reported in 1986 (Hernnstadt et al. *Bio/Technology* vol. 4, 305–308, 1986, U.S. Pat. No. 4,764,372, 1988). This strain, designated "*Bacillus thuringiensis* subsp. *san diego*", M-7, has been deposited at the Northern Regional Research Laboratory, USA under accession number NRRL B-15939. However, the assignee of the '372 patent, Mycogen, Corp. has publicly acknowledged that *Bacillus thuringiensis* subsp. *san diego* is *Bacillus thuringiensis* subsp. *tenebrionis*. Furthermore, the '372 patent has been assigned to Novo Nordisk A/S. Additionally, there has been disclosed a B.t. strain which is toxic against Lepidoptera and Coleoptera (PCT Application No. WO 90/13651). The toxin disclosed in PCT Application No. WO 90/13651 has a molecular weight of 81 kd.

During its sporulation cycle, B.t. produces a protein(s) in crystal form known as a crystal delta-endotoxin(s), having a molecular weight ranging from 27–140 kd, which upon ingestion kills insect larvae. Toxic activity may reside in one or more of such delta-endotoxins in a given B.t. strain. Most delta-endotoxins are protoxins that are proteolytically converted into smaller toxic (truncated) polypeptides in the target insect midgut (Höfte and Whiteley, 1989, *Microbiol. Rev.* 53:242–255). The delta-endotoxins are encoded by cry (crystal protein) genes. The cry genes have been divided into six classes and several subclasses based on structural similarities and pesticidal specificity. The major classes are Lepidoptera-specific (cryI); Lepidoptera-and Diptera-specific (cryII); Coleoptera-specific (cryIII); Diptera-specific (cryIV) (Höfte and Whiteley, 1989, *Microbiol. Rev.* 53:242–255); Coleoptera- and Lepidoptera-specific (referred to as cryV genes by Tailor et al., 1992, *Molecular Microbiology* 6:1211–1217); and Nematode-specific (referred to as cryV and cryVI by Feitelson et al., 1992, *Bio/Technology* 10:271–275) genes.

Delta-endotoxins have been produced by recombinant DNA methods. The delta-endotoxins produced by recombinant DNA methods may or may not be in crystal form.

B.t. delta-endotoxin is water insoluble except at alkaline pH, and is almost always plasmid encoded. Some strains of *Bacillus thuringiensis* have been shown to produce a heat-stable pesticidal adenine-nucleotide analog, known as β-exotoxin or thuringiensin, which is pesticidal alone (Sebesta et al., in H. D. Burges (ed.), *Microbial Control of Pests and Plant Diseases*, Academic Press, New York p. 249–281, 1981). β-exotoxin has been found in the supernatant of some *Bacillus thuringiensis* cultures. It has a molecular weight of 789 and is comprised of adenosine, glucose, and allaric acid (Lüthy et al., in Kurstak (ed.), *Microbial and Viral Pesticides*, Marcel Dekker, New York, 1982, pp. 35–72). Its host range includes, but is not limited to, *Musca domestica, Mamestra configurata* Walker, *Tetranychus urticae, Drosophila melanogaster,* and *Tetranychus cinnabarinus*. The toxicity of β-exotoxin is thought to be due to inhibition of DNA-directed RNA polymerase by competition with ATP. It has been shown that β-exotoxin is encoded by a Cry plasmid in five *Bacillus thuringiensis* (B.t.) strains and that β-exotoxin may be classified as type I or type II β-exotoxin (Levinson et al., 1990, *J. Bacteriol.* 172:3172–3179). β-exotoxin type I was found to be produced by B.t. subsp. *thuringiensis* serotype 1, B.t. subsp. *tolworthi* serotype 9, and B.t. subsp. *darmstadiensis* serotype 10. β-exotoxin type II was found to be produced by B.t. subsp. *morrisoni* serotype 8ab and is active against *Leptinotarsa decemlineata* (Colorado potato beetle). Other water soluble substances that have been isolated from B.t. include alpha-exotoxin which is toxic against the larvae of *Musca domestica* (Liuthy, 1980, *FEMS Microbiol. Lett.* 8:1–7); gamma-exotoxins, which are various proteolytic enzymes including lecithinases, chitinases, and proteases, the toxic effects of which are expressed only in combination with beta-exotoxin or delta-endotoxin (Forsberg et al., 1976,

*Bacillus thuringiensis: Its Effects on Environmental Quality*, National Research Council of Canada, NRC Associate Committee on Scientific Criteria for Environmental Quality, Subcommittees on Pesticides and Related Compounds and Biological Phenomena); sigma exotoxin which has a structure similar to beta-exotoxin, and is also active against *Leptinotarsa decemlineata* (Argauer et al., 1991, *J. Entomol. Sci.* 26:206–213); and anhydrothuringiensin (*Coll. Czechoslovak Chem. Comm.* 40, 1775, 1975).

WO 94/09630 discloses a water soluble substance that enhances the activity of *Bacillus thuringiensis* var. *kurstaki* and *Bacillus thuringiensis* var. *aizawai*.

Stonard et al. (1994, In Natural and Engineered Pest Management Agents, Paul A. Mann, Robert M. Hollingworth, eds., ACS, Washington, D.C., pp. 25–36) discloses diabroticins having the structure 1 R, $R_1$, $R_2$ = H, $R_3$ = OH Diabroticin A
2 R, $R_1$, $R_2$, $R_3$ = H Diabroticin B Diabroticins were isolated from B. subtilis and have activity against *Diabrotica undecimpunctata, Leptinotarsa decemlineata, Anthomus grandis* Boheman, mosquito larvae, *Staphylococcus aureus*, and *Micrococcus lutea*, but did not have activity against European corn borer, *Escherichia coli, B. subtilis*, and *Pseudomonas aeruginosa*. Activity against other pests were not disclosed in Stonard et al. Diabroticin A was also isolated from fermentation broths of *B. cereus*.

The art has strived to achieve increased mortality of B.t. formulations. Means have included searching for new strains with increased mortality, engineering present strains, and designing more effective formulations by combining B.t. spores and/or crystals with new pesticidal carriers or with chemical pesticides.

It is an object of the present invention to improve the insecticidal activity of known B.t. formulations.

It is also an object of the present invention to enhance the pesticidal activity of pesticides as well as find novel uses for known pesticidal products.

It is advantageous to isolate new strains of *Bacillus thuringiensis* to produce new substances so that there exists a wider spectrum of biopesticides for any given insect pest.

SUMMARY OF THE INVENTION

The invention is related to a novel *Bacillus thuringiensis* strain in which essentially all of the pesticidal activity of said strain is in the supernatant of a fermentation of said strain. Crystal protein and spores obtained from a fermentation of a *Bacillus thuringiensis* strain of the present invention do not possess any pesticidal activity. In a specific embodiment, the strain is selected from the group consisting of EMCC-0077 having the identifying characteristics of NRRL B-21090, or mutants thereof having substantially the same properties of EMCC-0077, EMCC-0078 having the identifying characteristics of NRRL B-21091, or mutants thereof having substantially the same properties of EMCC-0078, EMCC-0079 having the identifying characteristics of NRRL B-21092, or mutants thereof having substantially the same properties of EMCC-0079, EMCC-0080 having the identifying characteristics of NRRL B-21093, or mutants thereof having substantially the same properties of EMCC-0080, and EMCC-0081 having the identifying characteristics of NRRL B-21094, or mutants thereof having substantially the same properties of EMCC-0081.

A substance which has pesticidal activity against an insect pest of the order Coleoptera and acts together as, for example, a potentiator or synergizer with a different Bacillus related pesticide against a pest is obtained from a supernatant of a fermentation of said strain. In a preferred embodiment, said substance, has an $LC_{50}$ ($LC_{50}$ is the concentration of a given pesticidal substance required to kill 50% of the pests) of 126 µg of active ingredient/g of total material against *Leptinotarsa texana*. The $LC_{50}$ of the pellet of the fermentation of said strain is more than about 3000 µg of active ingredient/g of total material as assayed by bioassay.

In another embodiment, said substance has pesticidal activity against an insect pest of the order Coleoptera. In a most specific embodiment, said substance has pesticidal activity against an insect pest of the species *Diabrotica undecimpunctata, Leptinotarsa tewna, Anthomus grandia*, as well as surprisingly activity against an insect pest of the species *Ips calligraphus, Popillia japonicus, Epilachna varivastis, Leptinotarsa decemlineata*, and *Dendroctonus frontalis* of the order Coleoptera.

In a specific embodiment, said substance enhances the insecticidal activity of *Bacillus thuringiensis* crystal delta-endotoxin(s) against an insect pest(s). In a specific embodiment, said substance enhances the insecticidal activity of *Bacillus thuringiensis* subsp. *tenebrionis* crystal delta-endotoxin against an insect pest(s) of the order Coleoptera.

As defined herein, "a Bacillus related pesticide" is a Bacillus (e.g., *Bacillus thuringiensis* or *Bacillus subtilis*) strain or spore. A Bacillus related pesticide may also be a substance derived from Bacillus, e.g., protein or fragment thereof having activity against or which kill pests; a substance that provides plant protection, e.g., antifeeding substance; or a microorganism capable of expressing a Bacillus gene encoding a Bacillus protein or fragment thereof having activity against or which kill pests (e.g., *Bacillus thuringiensis* delta-endotoxin) and an acceptable carrier (see next section on Compositions). The pest may be, for example, an insect, a nematode, a mite, or a snail. A microorganism capable of expressing a Bacillus gene encoding a Bacillus protein or fragment thereof having activity against or which kill pests inhabiting the phyiloplane (the surface of the plant leaves), and/or the rhizosphere (the soil surrounding plant roots), and/or aquatic environments, and is capable of successfully competing in the particular environment (crop and other insect habitats) with the wild-type microorganisms and provide for the stable maintenance and expression of a Bacillus gene encoding a Bacillus protein or fragment thereof having activity against or which kill pests. Examples of such microorganisms include, but are not limited to, bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes, and Clostridium; algae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae; and fungi, particularly yeast, e.g., genera Saccharomyces, Cryptococcus, Kluyveromyces, Sporobolomyces, Rhodotorula, and Aureobasidium.

As defined herein, "pesticidal activity" measures the amount of activity against a pest through killing or stunting of the growth of the pest or protecting the plant from pest infestation.

The invention further relates to pesticidal compositions comprising the substance and a Bacillus related pesticide as well as methods of using the pesticidal compositions to control a pest.

The invention is further directed to a method for obtaining "substantially pure" substance of the present invention comprising the steps of (a) culturing a Bacillus thuringiensis strain on a suitable growth medium;

(b) recovering the supernatant of (a); and (c) subjecting the supernatant of step (b) to column chromatography to purify the substance.

As defined herein a "substantially pure" substance means a substance which contains less than 5% of contaminants, for example, delta-endotoxin protein.

BRIEF DESCRIPTION OF THE FIGURES

These and other features, aspects, and advantages of the present invention will become better understood with regard to the following description, appended claims, and accompanying figures where:

DETAILED DESCRIPTION OF THE INVENTION

Obtaining the Substance

Figure 1:
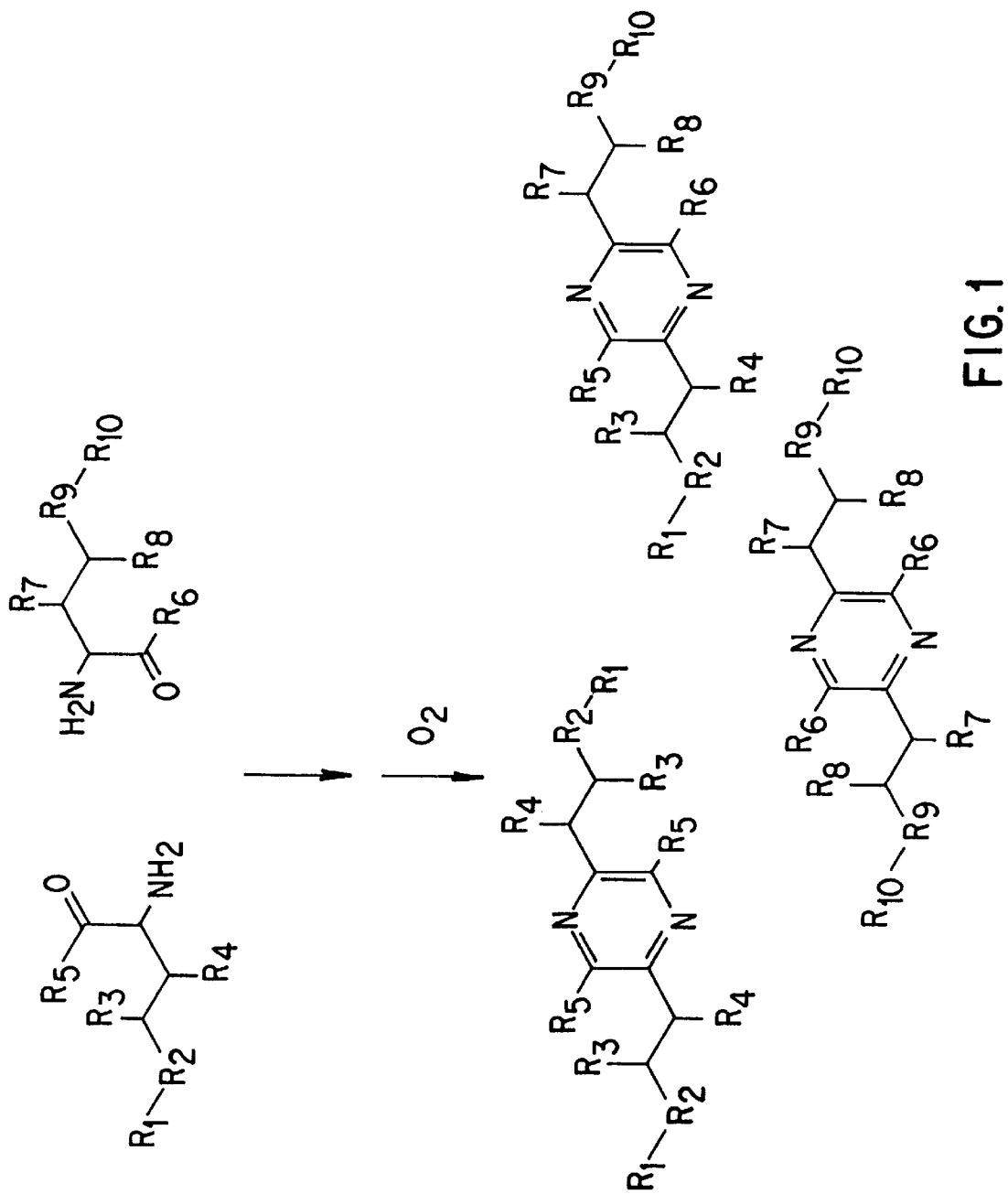
FIG. 1 shows a synthetic scheme for obtaining structure I.

The substance(s) may be obtained from the supernatant of a *Bacillus thuringiensis* fermentation including, but not limited to, the B.t. strains EMCC-0077 having the identifying characteristics of NRRL B-21090, or mutants thereof having substantially the same properties of EMCC-0077, EMCC-0078 having the identifying characteristics of NRRL B-21091, or mutants thereof having substantially the same properties of EMCC-0078, EMCC-0079 having the identifying characteristics of NRRL B-21092, or mutants thereof having substantially the same properties of EMCC-0079, EMCC-0080 having the identifying characteristics of NRRL B-21093, or mutants thereof having substantially the same properties of EMCC-0080, and EMCC-0081 having the identifying characteristics of NRRL B-21094, or mutants thereof having substantially the same properties of EMCC-0081.

The substance has activity against an insect pest(s) of the order Coleoptera and acts together with a Bacillus related pesticide as, e.g., a potentiator or synergizer. In a specific embodiment, the substance has the structure (I)

(I)

wherein $R_1$ is an amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen, $C_{1-5}$ alkoxy, or amino acid including but not limited to alanyl, valinyl, leucinyl, isoleucinyl, phenylalanyl, glycinyl, and phenylglycinyl;

$R_2$ is amino or alkyl ($C_{1-10}$);

$R_3$ is hydrogen, amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen, $C_{1-5}$ alkoxy, methyl amine, dimethyl amine, thionyl, methyl thionyl, cyano, or salt thereof including but not limited to phosphate, sulfate, acetate, carbonate and nitrate;

$R_4$ is hydrogen, amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen, $C_{1-5}$ alkoxy or salt thereof including but not limited to phosphate, sulfate, acetate, carbonate and nitrate;

$R_5$ is hydrogen, methoxy, amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen or $C_{1-5}$ alkoxy;

$R_6$ is hydrogen, amino, hydroxy, alkyl ($C_{1-10}$), alkyl, ester, halogen or $C_{1-5}$ alkoxy;

$R_7$ is hydrogen, amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen, $C_{1-5}$ alkoxy or salt thereof including but not limited to phosphate, sulfate, acetate, carbonate and nitrate;

$R_8$ is hydrogen, amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen, $C_{1-5}$ alkoxy, methyl amine, dimethyl amine, thionyl, methyl thionyl, cyano or salt thereof including but not limited to phosphate, sulfate, acetate, carbonate and nitrate;

$R_9$ is amino or alkyl ($C_{1-10}$); and $R_{10}$ is amino, hydroxy, alkyl ($C_{1-10}$), alkyl ($C_{1-10}$) ester, aryl (e.g., benzoyl, nitrobenzoyl, dinitrobenzoyl, halobenzoyl) ester, halogen, $C_{1-5}$ alkoxy, or amino acid including alanyl, valinyl, leucinyl, isoleucinyl, phenylalanyl, glycinyl, and phenylglycinyl.

The pyrazine nitrogens may optionally be substituted with alkyl ($C_{1-10}$), alkyl ($C_{1-10}$) ester, aryl (e.g., benzoyl, nitrobenzoyl, dinitrobenzoyl, halobenzoyl) ester, or oxygen.

It is to be understood that the invention extends to each of the stereoisomeric forms of the compounds of structure I as well as racemates.

In most specific embodiments, the substance has the structure Ia, hereafter referred to as "Ia" or Ib, hereafter referred to as "Ib".

Ia: R, R$_1$, R$_2$, R$_3$ = H
Ib: R, R$_1$, R$_2$ = H, R$_3$ = OH

*Bacillus thuringiensis* may be cultured using media and fermentation techniques known in the art (see, for example, Rogoff et al., 1969, J. Invertebrate Path. 14:122–129; Dulmage et al., 1971, J. Invertebrate Path. 18:353–358; Dulmage et al., in Microbial Control of Pests and Plant Diseases, H. D. Burges, ed., Academic Press, N.Y., 1980). Upon completion of the fermentation cycle, the supernatant can be recovered by separating B.t. spores and crystals from the fermentation broth by means well known in the art, e.g., centrifugation and/or ultrafiltration. Said substance is contained in the supernatant which may be recovered by means well known in the art, e.g., ultrafiltration, evaporation, and spray-drying.

Alternatively, the substance(s) of the present invention may be obtained by chemical synthesis using procedures known in the art.

To obtain structure I, the simple pyrazine ring with appropriate substitution and protecting groups can be formed by a number of reactions, for example, spontaneous condensation of alpha-aminocarbonyl compounds. A dihydropyrazine intermediate is formed but is readily oxidized with oxygen to the pyrazine. Dimerization of a single alpha-aminocarbonyl compound by this method would lead to a single pyrazine, whereas a reaction with two different alpha-aminocarbonyl compounds would lead to three products; said substance would be isolated by chromatographic separation (see FIG. 1). The latter reaction allows synthesis of pyrazines with different substituents off each side of the ring.

Purification of the substance(s) can be carried out by various procedures known in the art, including but not limited to chromatography (e.g., ion exchange, affinity, and size exclusion column chromatography), electrophoretic procedures, differential solubility, extraction, or any other standard technique known in the art (see, for example, *Protein Purification*, eds. J-C. Janson and Lars Ryden, VCH Publishers, New York, 1989).

The activity of said substance may be bioassayed using procedures known in the art, such as artificial diet incorporation, artificial diet overlay, leaf painting, leaf dip, and foliar spray. Specific examples of such bioassays are given in the Examples section, infra.

Compositions Comprising the Substance

Said substance can be formulated alone; along with a Bacillus related pesticide which as defined supra is a Bacillus strain, spore, protein or fragment thereof having activity against or which kills pests and optionally an acceptable carrier into an pesticidal composition(s) that is for example, a suspension, a solution, an emulsion, a dusting powder, a dispersible granule, a wettable powder, an emulsifiable concentrate, an aerosol or impregnated granule. Examples of such Bacillus strains include but are not limited to *Bacillus thuringiensis* subsp. *kurstaki* (marketed as DIPEL™ from Abbott Laboratories, Inc., JAVELIN™ from Sandoz, BIO-BIT™ from Novo Nordisk A/S, FORAY™ from Novo Nordisk A/S, MVP™ from Mycogen, BACTOSPEINE™ from Novo Nordisk A/S, and THURICIDE™ from Sandoz); *Bacillus thuringiensis* subsp. *aizawai* (marketed as FLORBAC™ from Novo Nordisk A/S, and XENTARI™ from Abbott Laboratories, Inc.); *Bacillus thuringiensis* subsp. *tenebrionis* (marketed as NOVODOR™ from Novo Nordisk A/S, TRIDENT™ from Sandoz, M-TRAK™ and M-ONE™ from Mycogen); *Bacillus thuringiensis* subsp. *israelensis* (marketed either as BACTIMOS™ or SKEETAL™ from Novo Nordisk A/S, TEKNAR™ from Sandoz, and VECTOBAC™ from Abbott Laboratories, Inc.); *Bacillus sphaericus* (marketed as SPHERIMOS™ from Novo Nordisk A/S); *Bacillus thuringiensis kurstaki/tenebrionis* (marketed as FOIL™ from Ecogen); *Bacillus thuringiensis kurstaki/aizawai* (marketed as CONDOR™ from Ecogen and AGREE™ from Ciba-Geigy); and *Bacillus thuringiensis kurstaki/kurstaki* (marketed as CUTLASS™ from Ecogen). The Bacillus related protein may be selected from the group including but not limited to CryI, CryII, CryIII, CryIV, CryV, and CryVI.

Said substance may also be formulated with other factors or substances obtained from the supernatant of a Bacillus supernatant including but not limited to an exotoxin and/or the enhancing factor disclosed in application Ser. No. 08/095,240, filed Jul. 20, 1993, incorporated herein by reference. Optionally, the formulation may also comprise a Bacillus related pesticide, chemical pesticide and/or a virus with pesticidal properties and an acceptable carrier.

In a specific embodiment, the components of said composition may act in a synergistic fashion. As a result, said composition may have greater efficacy than can be attained with each individual component. Synergism may also be manifested by equal or greater efficacy with lower and/or less frequent doses than would be required for each individual component. Alternatively, said substance may act to enhance a Bacillus related pesticide.

In compositions comprising the substance and a Bacillus related pesticide, the substance is present in the amount of about 0.001 to about 300 g per LTU. As defined herein, "LTU" is a *Leptinotarsa texana* unit as determined by bioassay. The bioassay compares the sample to a standard Bacillus reference material using *Leptinotarsa texana* or other pest as the standard test organism. The potency is determined by dividing the reference standard LC$_{50}$ then multiplying by the reference standard potency.

In another embodiment, the composition may comprise said substance in substantially pure form or a supernatant from Bacillus in dry, concentrated, or liquid form and a suitable pesticidal carrier, examples of which are disclosed infra. This composition may be applied separately to a plant, e.g., transgenic plants. Specifically, the composition may be applied to a plant previously containing a *Bacillus thuringiensis* gene. In another embodiment, the composition may be applied to a plant previously exposed to a *Bacillus thuringiensis* composition. The substance is present in the composition at a concentration of from about 0.001% to about 60% (w/w).

Such compositions disclosed above may be obtained by the addition of a surface active agent, an inert carrier, a preservative, a humectant, a feeding stimulant, an attractant, an encapsulating agent, a binder, an emulsifier, a dye, a U.V. protectant, a buffer, a flow agent, or other component to facilitate product handling and application for particular target pests.

Suitable surface-active agents include but are not limited to anionic compounds such as a carboxylate, for example, a metal carboxylate of a long chain fatty acid; an N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl-naphthalene sulphonate; salts or sulphonated naphthalene-formaldehyde condensates; salts of sulphonated phenol-formaldehyde condensates; or more complex sulphonates such as the amide sulphonates, e.g., the sulphonated condensation product of oleic acid and N-methyl taurine or the dialkyl sulphosuccinates, e.g., the sodium sulphonate or dioctyl succinate. Non-ionic agents include but are not limited to condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitol fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate;

an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, mica, gypsum, fertilizer, phyllosilicates, carbonates, sulfates, or phosphates; organic materials such as sugar, starches, or cyclodextrins; or botanical materials such as wood products, cork, powdered corncobs, rice hulls, peanut hulls, and walnut shells.

The compositions of the present invention can be in a suitable form for direct application or as a concentrate or primary composition which requires dilution with a suitable quantity of water or other diluent before application. The pesticidal concentration will vary depending upon the nature of the particular formulation, specifically, whether it is a concentrate or to be used directly. The composition contains 1 to 98% by weight of a solid or liquid inert carrier, and 0 to 50%, preferably 0.1 to 50% of a surfactant. These compositions will be administered at the labeled rate for the commercial product, preferably about 0.01 pound to 5.0 pounds per acre when in dry form and at about 0.01 pint to 25 pints per acre when in liquid form.

In a further embodiment, the Bacillus related pesticide and/or substance can be treated prior to formulation to prolong the pesticidal activity when applied to the environment of a target pest as long as the pretreatment is not deleterious to the Bacillus related pesticide or substance. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropranol and ethanol; and histological fixatives, such as Bouin's fixative and Helly's fixative (see, for example, Humason, Animal Tissue Techniques, W.H. Freeman and Co., 1967).

The compositions of the invention can be applied directly to the plant by, for example, spraying or dusting at the time when the pest has begun to appear on the plant or before the appearance of pests as a protective measure. Plants to be protected within the scope of the present invention include but are not limited to cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (e.g., linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamentals. The substance may be applied by foliar, furrow, broadcast granule, "lay-by", or soil drench application. It is generally important to obtain good control of pests in the early stages of plant growth as this is the time when the plant can be most severely damaged. The spray or dust can conveniently contain another pesticide if this is thought necessary. In a preferred embodiment, the composition of the invention is applied directly to the plant.

The compositions of the present invention may be effective against pests of the order Coleoptera, e.g., Leptinotarsa sp. (e.g., *Leptinotarsa texana, Leptinotarsa decemlineata*), *Diabrotica undecimpunctata, Dendroctonus frontalis, Anthonomus grandis, Acanthoscelides obtectus, Callosobruchus chinensis, Epilachna varivestis, Pyrrhalta luteola, Cylas formicarius elegantulus, Listronotus oregonensis*, Sitophilus sp., *Cyclocephala borealis, Cyclocephala immaculata, Macrodactylus subspinosus, Popillia japonica, Rhizotrogus majalis, Alphitoblus diaperinus, Palorus ratzeburgi, Tenebrio molitor, Tenebrio obscurus, Tribolium castaneum, Tribolium confusum, Tribolius destructor*. The compositions of the invention may also be effective against insect pests including but not limited to pests of the order Lepidoptera, e.g., *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis*, Archips sp., Argyrotaenia sp., *Athetis mindara, Bombyx mori, Bucculatrix thurberiella, Cadra cautella*, Choristoneura sp., *Cochylls hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis*, Malacosoma sp., *Mamestra brassicae, Mamestra configurata, Manduca quinquemaculata, Manduca sexta, Maruca testulalis, Melanchra picta, Operophtera brumata*, Orgyia sp., *Ostrinia nubilalis, Paleacrita vernata, Papilio cresphontes, Pectinophora gossypiella, Phryganidia californica, Phyl-* lonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonota ocellana, Spodoptera sp., Thaurnstopoea pityocampa, Tineola bisselliella, Trichoplusia ni, Udea rubigalis, Xylomyges curialis, Yponomeuta padella; Diptera, e.g., Aedes sp., Andes vittatus, Anastrepha ludens, Anastrepha suspensa, Anopheles barberi, Anopheles quadrimaculatus, Armigeres subalbatus, Calliphora stygia, Calliphora vicina, Ceratitis capitata, Chironomus tentans, Chrysomya rufifacies, Cochliomyia macellaria, Culex sp., Culiseta inornata, Dacus oleae, Delia antigua, Delia platura, Delia radicum, Drosophila melanogaster, Eupeodes corollae, Glossina austeni, Glossina brevipalpis, Glossina fuscipes, Glossina morsitans centralis, Glossina moristans morsitans, Glossina moristans submorsitans, Glossina pallidipes, Glossina palpalis gambiensis, Glossina palpalis palpalis, Glossina tachinoides, Haemagogus equinus, Haematobius irritans, Hypoderma bovis, Hydoderma lineatum, Leucopis ninae, Lucilia cuprina, Lucilia sericata, Lutzomyia longlpaipis, Lutzomyia shannoni, Lycoriella mali, Mayetiola destructor, Musca autumnalis, Musca domestica, Neobellieria sp., Nephrotoma suturalis, Ophyra aenescens, Phaenicia sericata, Phlebotomus sp., Phornia regina, Sabethes cyaneus, Sarcophaga bullata, Scatophaga stercoraria, Stomaxys calcitrans, Toxorhynchites amboinensis, Tripteroides bambusa; Acari, e.g., Oligonychus pratensis, Panonychus ulmi, Tetranychus urticae; Hymenoptera, e.g., Iridomyrrnex humilis, Solenopsis invicta; Isoptera, e.g., Reticulitermes hesperus, Reticuliternes flavipes, Coptotermes formosanus, Zootermopsis angusticollis, Neotermes connexus, Incisiterrnes minor, Incisitermes immigrans; Siphonaptera, e.g., Ceratophyllus gallinae, Ceratophyllus niger, Nosopsyllus fasciatus, Leptopsylla segnis, Ctenocephalides canis, Ctenocephallldes felis, Echicnophaga gallinacea, Pulex irritans, Xenopsylla cheopis, Xenopsylla vexabilis, Tunga penetrans; and Tylenchida, e.g., Melodidogyne incognita, Pratylenchus penetrans.

The following examples are presented by way of illustration, not by way of limitation.

EXAMPLES

Example 1

Cultivation of Various B.t. Isolates

Subcultures of EMCC-0077, EMCC-0078, EMCC-0079, EMCC-0080, and EMCC-008 1, maintained on a Nutrient Broth Agar slants, are used to inoculate 250 ml baffled shake flasks containing 50 ml of medium with the following composition.

| | |
|---|---|
| Corn Steep liquor | 15 g/L |
| Maltrin-100 | 40 g/L |
| Potato Starch | 30 g/L |
| $KH_2PO_4$ | 1.77 g/L |
| $K_2HPO_4$ | 4.53 g/L |

The pH of the medium is adjusted to 7.0 using 10 N NaOH.

After inoculation, shake flasks are incubated at 300C on a rotary shaker at 250 rpm for 72 hours. The whole culture broths are used for testing against Diabrotica indecimpunctata.

Example 2

Diabrotica undecimpunctata Activity In Whole Culture Broth From Various B.t. Isolates 2.5 ml of the whole culture broths obtained from the above fermentation are removed and transferred from the shake flasks into 50 ml polypropylene bioassay tubes. Diabrotica undecimpunctata diet is added into each tube to a final volume of 25 ml. The diet and the testing material is then mixed vigorously and dispensed into bioassay trays for bioassay. Three to six eggs of Diabrotica undecimpunctata are applied on the surface of the "diet". Mylar is ironed onto the bioassay trays and the trays are incubated at 28° C. without photoperiod. Scoring is carried out at 7 days. Mortality is scored on the 7th day after incubation. SS7=the size of dead larvae on the 7th day when compared with the live, control larvae on the same day as SS7 of 4. SS7=3, SS7=2, and SS7=1 represent the size of the larvae as 75%, 50%, & 25% respectively of the live, control larvae of 4.

The results are shown below in TABLE 1. These results indicate that in all 5 strains tested there was 100% mortality. Furthermore, the dead larvae were 12.5% of the size of the live control larvae.

TABLE 1

Diabrotica undecimpunctata Activity in Whole Culture Broths

| Strain | % Mortality | S57 |
|---|---|---|
| EMCC-0077 | 100 | 0.5 |
| EMCC-0078 | 100 | 0.5 |
| EMCC-0079 | 100 | 0.5 |
| EMCC-0080 | 100 | 0.5 |
| EMCC-0081 | 100 | 0.5 |

Example 3

Localization of Diabrotica undecimpunctata Activity

In order to test whether the Diabrotica undecimpunctata activity is associated with the delta-endotoxin/spores or the supernatant, 2.5 ml of the whole culture broths from EMCC-0077, EMCC-0080, EMCC-0081, and NB 125 (a Bacillus thurigiensis subsp. tenebrionis grown under the identical conditions) is centrifuged in a Sorvall RC-5B centrifuge at 15,000 rpm (Sorvall SS34 rotor) for 15 minutes to separate the supernatant and the pellet. The crystal delta-endotoxins plus the spores are recovered in the pellet. The delta-endotoxins produced by the Diabrotica undecimpunctata-active B.t. isolate EMCC-0077 have molecular weights of 66 kD, 29 kD and 12 kD as determined by SDS-PAGE. The delta-endotoxins produced by the Diabrotica undecimpunctata-active B.t. isolate EMCC-0078 have molecular weights of 153 kD, 77 kD, 67 kD, 61 kD, 50 kD, 42 kD, 34 kD, 30 kD, 24 kD as determined by SDS-PAGE. The delta-endotoxins produced by the Diabrotica undecimpunctata-active B.t. isolate EMCC-0079 have a molecular weight of 135–145 kD, as determined by SDS-PAGE. The delta-endotoxins produced by the Diabrotica undecimpunctata-active B.t. isolate EMCC-0080 have molecular weights of 94 kD and 40 kD, as determined by SDS-PAGE. The delta-endotoxins produced by the Diabrotica undecimpunctata-active B.t. isolate EMCC-0081 have molecular weights of 129 kD and 32 kD as determined by SDS-PAGE.

Each supernatant (2.5 ml) obtained from the above centrifugation is transferred into a 50 ml polypropylene bioassay tube. The pellet is then resuspended into 2.5 ml of sterile distilled water and transferred into a separate 50 ml polypropylene bioassay tube. Diabrotica undecimpunctata diet is then added into bioassay tubes which contained either the supernatant or the resuspended pellet to a final volume of 25 ml. The remaining steps of bioassay are identical to those described above. The scoring is also the same as described above.

The results as seen in TABLE 2 show that the *Diabrotica undecimpunctata* activity from EMCC-0077, EMCC-0080, and EMCC-0081 is present in all of the supernatants, whereas the minor *Diabrotica undecimpunctata* activity from the known *Bacillus thuringiensis* subsp. *tenebrionis* is concentrated in the pellet (spore plus crystal).

TABLE 2

*Diabrotica undecimpunctata* Activity in Supernatant and Pellet

| Strain | Fraction | % Mortality | Stunt Score |
|---|---|---|---|
| EMCC-0077 | Supernatant | 100 | 0.5 |
|  | Pellet | 10 | 3.0 |
| EMCC-0080 | Supernatant | 100 | 0.5 |
|  | Pellet | 0 | 4.0 |
| EMCC-0081 | Supernatant | 100 | 0.5 |
|  | Pellet | 0 | 3.0 |
| NB125 | Supernatant | 0 | 3.0 |
|  | Pellet | 50 | 1.5 |

Example 4

Activity Against *Leptinotarsa texana*

After filtration through a 0.2 μ membrane, the supernatant of EMCC-0080, obtained from Example 1, is used to assay for beetle activity.

The filtered supernatant is applied to eggplant foliage at a volume of 20 GPA (gallons per acre). Dilutions are 0, 1:1, 1:4, 1:8 (supernatant:deionized water, v/v).

*Leptinotarsa texana* larvae are exposed to the treated foliage following standard protocol. Each plant is loaded with 20 larvae of *Leptinotarsa texana*.

The results as tabulated in TABLE 3 below show that the filtered supernatant of EMCC-0080 is active against *Leptinotarsa texana*.

TABLE 3

*Leptinotarsa taxana* Activity in EMCC-0080

| Strain | Dilution | % Mortality |
|---|---|---|
| EMCC-0080 | 0 | 95 |
|  | 1:1 | 55 |
|  | 1:4 | 20 |
|  | 1:8 | 0 |
| Untreated Control |  | 0 |

Example 5

Synergistic Effect of EMCC-0080 and NOVODOR™

The results shown in TABLE 3, supra, indicate that the supernatant of EMCC-0080 is not active at 1:8 dilution (v/v) alone. However, when the eggplant foliage is treated with 1.25% or 2.5% of 10× concentrated EMCC-0080 supernatant plus 200 μg of NOVODOR™ (Novo Nordisk A/S, Bagsvaerd, Denmark) per ml, a synergistic effect is obtained as evidenced by the sharp decline of the $LC_{50}$ and $LC_{90}$ of NOVODOR™. The data is presented in TABLE 4 below.

TABLE 4

Synergistic Effect of EMCC-0080 and NOVODOR™

| Sample | $LC_{50}$ (μg/g)[1] | $LC_{90}$ (μg/g)[2] | Slope[3] |
|---|---|---|---|
| NOVODOR™ | 642 | 4,286 | 1.55 |
| NOVODOR™ + 1.25% EMCC-0080 | 250 | 1,292 | 1.79 |
| NOVODOR™ + 2.5% EMCC-0080 | 98 | 490 | 1.83 |

[1] $LC_{50}$ is defined as the concentration which kills 50% of the targeted insect population.
[2] $LC_{90}$ is defined as the concentration which kills 90% of the targeted insect population.
[3] The slope refers to the slope of a % mortality v. log concentration curve.

Example 6

Purification of Coleopteran-Active Substance Produced By B.t. Strain EMCC-0080

B.t. strain EMCC-0080 is grown for 24 hours at 30° C. in a medium with the following composition in grams per liter at pH 7.0:

| Maltodextrin | 40 g |
|---|---|
| Soy Protein | 40 g |
| $KH_2PO_4$ | 1.8 g |
| $K_2HPO_4$ | 4.5 g |
| $MgSO_4$—$7H_2O$ | 0.3 g |
| Trace metals | 0.2 ml |

Cells and other insolubles are removed from the whole culture broth of B.t. strain EMCC-0080 by centrifugation followed by filtration of the resulting supernatant through Celite and a 0.2 μ membrane. The resulting permeate is then concentrated 10-fold by evaporation.

The purification of the coleopteran-active substance(s) from the 10× concentrated permeate is achieved using a four step purification procedure. During purification, activity is monitored by a *Diabrotica undecimpunctata* surface bioassay as described infra, and purity is determined by capillary electrophoresis as described in EXAMPLE 8. All chromatographic steps employ detection at 226 nm.

Specifically, the surface bioassay is conducted as follows. Samples of the 10× concentrated permeate are applied to individual wells of a microtiter plate containing 200 μl of solidified artificial insect diet per well, and then air dried. Two to four neonates of *Diabrotica undecimpunctata* (corn rootworm, CRW) are gently placed in each well with a paintbrush. The microtiter plates are then sealed with Mylar punched with holes for air exchange and are incubated at 30° C. and 80% humidity. Scoring for percent mortality is carried out at 5 days.

In the first step, the 10× concentrated permeate is first purified by Pharmacia SP Sephadex® C-25 (cation exchange) column chromatography (5×30 cm). A 450 ml sample of the 10× concentrated permeate is diluted to 18 liter with deionized water, loaded onto the column which is pre-equilibrated with 20 mM ammonium acetate buffer at pH 5.0. The column is eluted at 18 mnl per minute with a 5.0 liter continuous gradient from 20 mM to 0.5M ammonium acetate buffer at pH 5.0. Fractions of 10 ml are collected, bioassayed, and examined for purity. The active fractions are pooled (approximately 150 ml), lyophilized, and redissolved in deionized water to approximately ⅕ the original volume.

In the second step, a 25 ml sample from the first step is loaded onto a BioRad P2 (extra fine) size exclusion column (5×100 cm) which is pre-equilibrated with deionized water. The column is eluted at a flow rate of 1 ml per minute with deionized water. Fractions of 10 ml are collected, bioassayed, and examined for purity by capillary electrophoresis. The active fractions are pooled (approximately 400 ml).

In the third step, the 400 ml pool from the second step is diluted to 16 liters with deionized water. The solution is loaded onto a Pharmacia S Sepharose® Fast Flow (strong cation exchange) column (5×30 cm) which is pre-equilibrated with 20 mM ammonium acetate buffer at pH 5.0. The column is eluted at a flow rate of 17 ml per minute with a 5.0 liter continuous gradient from 20 mM to 0.5 M ammonium acetate buffer at pH 5.0. Fractions of 20 ml are collected, bioassayed, and examined for purity. The active fractions are pooled (approximately 250 ml) and then lyophilized to dryness to remove the volatile ammonium acetate buffer.

In the fourth step, the lyophilized pool from third step is dissolved in 400 ml deionized water. The solution is loaded onto a BioRad Chelex® 100 column (0.9×30 cm) which was pre-equilibrated with 20 mM ammonium formate buffer at pH 4.0. The column is eluted at a flow rate of 5 ml per minute with a 2.4 liter step gradient from $0.02 \rightarrow 0.1 \rightarrow 0.2 \rightarrow 0.35 \rightarrow 0.5 \rightarrow 1.0$ M ammonium formate buffer at pH 4.0. Fractions of 20 ml are collected, bioassayed, and examined for purity. The active fractions are pooled (approximately 300 ml) and then lyophilized to dryness to remove the volatile ammonium formate buffer.

Capillary electrophoresis shows the purified coleopteran-active material comprises two compounds, Ia and Ib.

Example 7

Structure Elucidation of Coleopteran-Active Substances

The structures of compounds Ia and Ib are elucidated from the spectroscopic data collected on their acetylated derivatives (Derivatives A and B).

A 114 mg mixture of Ia and Ib is acetylated in 5.0 ml pyridine with 5.0 ml 1 0 acetic anhydride and a crystal of 4-dimethylaminopyridine as a catalyst for 24 hours at room temperature, and then purified by semi-preparative RP-$C_{18}$ HPLC. A 5 mg sample in 25 µl is loaded onto the column and eluted at 4 ml per minute with 80% water-20% acetonitrile.

Detection is at 254 nm.

NMR spectroscopic data collected on Derivative A indicates the presence of 14 carbons and 17 protons. However, mass spectral data suggests a molecular weight of 652 and a formula of $C_{28}H_{40}N_6O_{12}$ (exact mass, 653.2801, MH+, calc. 653.2782). Therefore, the compound is determined to be symmetrical where only half of the signals are observed by NMR.

Several spin systems are observed by NMR. A central pyrazine ring substituted in the 2 and 5 positions is indicated by the high field proton singlets at 8.6 ppm (H-3 and H-6) which shows long range couplings to all of the carbons in the ring and to the first carbon of the side chain (C-7). The side chain of three carbons is acetylated at both position 7 and 8 with a methylene at position 9. Carbon 9 is found to have a long range correlation to the carbonyl of an ester, and the ester is determined to be part of an alanine which is acetylated at the amino group.

The structure of Derivative B differs in one position from Derivative A. In one of the side chains of Derivative B, the C-7 carbon no longer is acetylated or attached to oxygen, but is found to be a methylene. The other side chain is identical to that in Derivative A. This difference of only one oxygen is also observed in the mass spectral data. Mass spectral data is obtained with an exact mass of 595.2722 (MH+, calc. 595.2727) for Derivative B, indicating a formula of $C_{26}H_{38}N_6O_{10}$. The optical densities of Derivatives A and B are as follows:

Derivative A $[\alpha]_D^{27}=-6.9°$ C. and Derivative B $[\alpha]_D^{27}=+32°$ C. Full assignments of the $^1H$ and $^{13}C$ NMR data are made on the basis of decoupling experiments, COSY, HMQC and HMBC. The assignments are presented in TABLE 5.

TABLE 5

$^1H$ and $^{13}C$ NMR data of Derivative A and Derivative B in D-4 methanol

| Pos-ition | $^1H$ (mult., integ., coupling constants) | | $^{13}C$ | |
|---|---|---|---|---|
| | Derivative A | Derivative B | A | B |
| 2 | | | 152.9 | 154.7 |
| 3 | 8.6(s, 1H) | 8.54(s, 1H) | 144.2 | 144.4 |
| 5 | | | 152.9 | 151.1 |
| 6 | 8.6(s, 1H) | | 144.2 | 145.6 |
| 7 | 5.84(d, 1H, J=7.4Hz) | 2.95(dd, 1H, J=13.9, 9.2) 3.10(dd, 1H, J=13.9, 4.8) | 74.0 | 37.5 |
| 8 | 4.72(m, 1H) | 4.48(m, 1H) | 52.1 | 50.2 |
| 9 | 4.24(dd, 1H, J=11.5, 6.7Hz) 4.30(dd, 1H, J=11.5, 6.7Hz) | 4.11(dd, 1H, J=11.4, 6.7) 4.20(m, 1H) | 63.5 | 66.3 |
| 10 | | | 174.8† | 174.7 |
| 11 | 4.20(q, 1H, J=7.1Hz) | 4.20(m, 1H) | 50.3 | 49.8 |
| 12 | 1.2(d, 3H, J=7.1Hz) | 1.17(d, 3H, J=7.3) | 17.8 | 18.1 |
| 13 | 5.84(d, 1H, J=7.4Hz) | 5.80(d, 1H, J=7.4) | 74.0 | 73.9 |
| 14 | 4.72(m, 1H) | 4.70(m, 1H) | 52.1 | 52.1 |
| 15 | 4.24(dd, 1H, J=11.5, 6.7Hz) 4.30(dd, 1H, J=11.5, 6.7) | 4.20(m, 1H) 4.30(dd, 1H, J=11.6, 6.8) | 63.5 | 63.6 |
| 16 | | | 174.8† | 174.7 |
| 17 | 4.20(q, 1H, J=7.1Hz) | 4.20(m, 1H) | 50.3 | 50.4 |
| 18 | 1.2(d, 3H, J=7.1Hz) | 1.20(d, 3H, J=7.3Hz) | 17.8 | 17.8 |
| 19 | | | 171.4† | 171.4 |
| 20 | 2.1* | 1.97 | 20.6** | 20.6 |
| 21 | | | 172.9† | 172.4 |
| 22 | 2.0* | 2.02 | 20.5** | 22.5 |
| 23 | | | 172.3† | 172.5 |
| 24 | 1.95* | 2.09 | 22.5** | 22.6 |
| 25 | | | 172.3† | 172.9 |
| 26 | 1.95* | 2.03 | 22.5** | 20.7 |
| 27 | | | 172.9† | 171.4 |
| 28 | 2.0* | 1.95 | 20.5** | 20.6 |
| 29 | | | 171.4† | |
| 30 | 2.1* | | 20.6** | |

*, **, † — signals may be interchanged

Mass spectral data for the mixture of compounds Ia and Ib give two molecular ions of 400 and 384. From this data, it is determined that the molecular formula of compound Ia is $C_{16}H_{28}N_6O_6$ and compound Ib is $C_{16}H_{28}N_6O_5$. The structures of Ia and Ib are determined by comparing the NMR data of Derivative A and Derivative B with the NMR data of the mixture of Ia and Ib. The structures of Ia and Ib are shown below.

Ia: R, $R_1$, $R_2$, $R_3$ = H
Ib: R, $R_1$, $R_2$ = H, $R_3$ = OH

The properties of compounds Ia and Ib and their acetylated derivatives are summarized below:

| Derivative A: | Molecular weight: | 652 |
| --- | --- | --- |
| | Empirical formula: | $C_{28}H_{40}N_6O_{12}$ |
| | UV(MeOH): | 275, 310 nm |
| | MS(FAB): | (M + H) m/z 653.2801, calc. 653.2782 |
| Derivative B: | Molecular weight: | 594 |
| | Empirical formula: | $C_{26}H_{38}N_6O_{10}$ |
| | UV(MeOH): | 275, 310 nm |
| | MS(FAB): | (M + H) m/z 595.2722, calc. 595.2727 |
| Ia: | Molecular weight: | 400 |
| | Empirical formula: | $C_{16}H_{28}N_6O_6$ |
| | UV($H_2O$): | 275, 310 nm |
| | MS(FAB): | (M + H) 401 |
| Ib: | Molecular weight: | 384 |
| | Empirical formula: | $C_{16}H_{28}N_6O_5$ |
| | UV($H_2O$): | 275, 310 nm |
| | MS(FAB): | (M + H) 385 |

Example 8

Quantitation of Compounds Ia and Ib in Fermentation Broths

B.t. strain EMCC-0080 is grown as described in EXAMPLE 1. The concentration of compounds Ia and Ib in the fermentation broth is determined by capillary electrophoresis.

Specifically, a BioRad Biofocus 3000 Capillary Electrophoresis System equipped with an uncoated capillary (50 μm×50 cm), 0.1M phosphate at pH 2.5, voltage at 20 KV, positive to negative polarity, and detection at 200 nm is used for quantification. The sample volume is 30 μl with a 5 psi second injection. The analysis time is 10 minutes with the coleopteran-active compounds Ia and Ib eluting at 6.0 and 5.9 minutes, respectively.

Alternatively, a Beckman P/ACE 2100 Capillary Electrophoresis System equipped with an uncoated capillary (50 μm×47 cm), 0.1M phosphate buffer at pH 2.5, voltage at 20 KV, positive to negative polarity, and detection at 200 nm is used for quantification. The sample volume is 30 μl with a 10 second pressure injection. The analysis time is 10 minutes with the coleopteran-active compounds Ia and lb eluting at 7.0 and 6.7 minutes, respectively.

Cells and other insolubles are removed from the whole culture broth of B.t. strain EMCC-0080 by centrifugation and by filtration through Celite and a 0.2 membrane. The 2 0 resulting supernatant is analyzed by capillary electrophoresis as described above. The results indicated that coleopteran-active compounds Ia and lb are each present at a level of approximately 90 mg per liter culture broth.

Example 9

Potency Determination of Compounds Ia and Ib

The relative potency of a crude mixture of compounds Ia and Ib (approximately 1:1 w/w) is determined using *Leptinotarsa texana* as the test insect and comparing mortality associated with an internal standard preparation of *Bacillus thuringiensis* subsp. *tenebrionis*.

Foliar bioassays are performed to determine the potency of a crude mixture of compounds Ia and Ib against *Leptinotarsa texana*. To perform the foliar bioassay, test materials and standards are weighed into 50 ml centrifuge tubes and suspended with deionized water containing 0.1% Tween® 20. 1,200 mg of *Bacillus thuringiensis* subsp. *tenebrionis* standard are weighed out and suspended to give a final concentration of 12,000 μg/g. The test samples (i.e., NOVODOR™ and NOVODOR™ with compounds Ia and Ib) are treated in a similar fashion unless a rate finding bioassay has shown that the delivered dosage is too high or too low to result in a sufficient number of valid data points. If this is the case, the concentration of the primary stock solution is increased or decreased by changing the amount of diluent added to the stock solution. Each sample is then homogenized for 30 seconds using a Virtis Homogenizer, and sonicated for 20 seconds at 100 Watts using a Braunsonic 1510 ultrasonic homogenizer. Each of these stock solutions are then diluted using a Hamilton Microlab 1000 to give seven serial dilutions consisting of 3,000, 2,000, 1333, 857, 545, 364, and 245 μg/ml in a total of 16 ml. Each of these 16 ml solutions are applied to approximately 288 square inches of eggplant leaves using a Devries Linear Track sprayer calibrated to deliver 20 gallons per acre. Control leaves are sprayed with 16 ml deionized water. Leaves are air dried and then placed over the rim of a one ounce clear plastic cup containing 5 second instar *Leptinotarsa texana* larvae. Cardboard lids are then placed over the leaf and the lid is pressed into place, cutting a 4 cm leaf disk and sealing it inside the cup. The cups are then inverted and the larvae dropped onto the leaf's treated surface. Eight cups are prepared for each one of the seven serial dilutions. The cups are taped together, labeled, placed on racks, and incubated for 3 days at 30° C. and 65% relative humidity. These 56 experimental cups and 8 control cups constitute one bioassay.

After three days, insect mortality is rated. Each cup is given a sharp blow and larvae that did not move are counted as dead. Percent mortality is calculated, and the data are analyzed via parallel probit analysis. $LC_{50}$s, $LC_{90}$s, slope of the regression lines, coefficient of variation, and potencies are estimated.

To determine the potency, a crude mixture of compounds Ia and Ib is diluted, bioassayed, and compared to a *Bacillus thuringiensis* subsp. *tenebrionis* standard which is assigned a potency of 20,000 LTU/gram (*Leptinotarsa texana* Units/gram).

The potency results are presented in TABLE 6, infra, and indicate that the crude mixture of compounds Ia and Ib (1:1 w/w) has a potency of 75,555 LTU per g active ingredient with an $LC_{50}$ of 70 ug per ml (1.8 mg total active ingredient per ml).

TABLE 6

| Potency of a mixture of compounds Ia and Ib | | |
| --- | --- | --- |
| Sample | $LC_{50}$ μg/ml | Estimated potency |
| Ia/Ib Mixture | 70 | 75,555 LTU |

Example 10

Potentiation of *Bacillus thuringiensis* subsp. *tenebrionis* Crystal Delta-Endotoxin with Compounds Ia and Ib The ability of compounds Ia and Ib to potentiate the insecticidal activity of the crystal delta-endotoxin from

*Bacillus thuringiensis* subsp. *tenebrionis* against *Leptinotarsa texana* was determined by adding a crude mixture of compounds Ia and Ib to NOVODOR™, and measuring the $LC_{50}$s via parallel probit analysis.

Foliar bioassays are performed against Leptinotarsa texana as described in EXAMPLE 9 to determine the level of potentiation gained by adding compounds Ia and Ib to NOVODOR™. A crude mixture of compounds Ia and Ib is added to NOVODOR™. Solutions are serially diluted using the Hamilton Microlab 1000 to give stock solutions containing NOVODOR™ at 1000.0, 666.7, 444.4, 285.7, 181.8, 121.2, and 80.0 µg/g. Two different dilutions of a mixture of Ia and Ib are prepared resulting in seven serial dilutions containing 72.0, 48.0, 32.0, 20.6, 13.1, 8.7, and 5.8 µg/g (2.5% v/v with 1000 µg/g NOVODOR™); and 36.0, 24.0, 16.0, 10.3, 6.5, 4.4, and 2.9 µg/g (1.25% v/v with 1000 µg/g NOVODOR™). Neat samples (without compounds Ia and Ib) and reference substances are prepared as well. The $LC_{50}$s of the paired neat samples are divided by the potentiated $LC_{50}$ values to give the fold reduction in $LC_{50}$ associated with the mixture of compounds Ia and Ib.

The results are presented in TABLE 7, infra, and indicate that the crude mixture of compounds Ia and Ib potentiates the insecticidal activity of NOVODOR™ against *Leptinotarsa texana*.

TABLE 7

Potentiation of NOVODOR ™ With a Mixture of Compounds Ia and Ib Against *Leptinotarsa texana*

| Sample | $LC_{50}$ µg/ml | Potentiation Factor |
| --- | --- | --- |
| NOVODOR ™ | 642 | 0 |
| NOVODOR ™ + 1.25% Ia/Ib | 250 | 2.6 |
| NOVODOR ™ + 2.50% Ia/Ib | 98 | 6.5 |

Example 11

Activity of a Mixture of Compounds Ia and Ib Against Beetles *Ips calligraphus* and *Dendroctonus frontalis*

The toxicity of a crude mixture of compounds Ia and Ib is determined against the beetles *Ips calligraphus* and *Dendroctonus frontalis*. 3 ml of a crude solution of compounds Ia and Ib (1.8 mg active ingredient per ml) are added to 5 grams of freeze dried Lobolly pine phloem and 7 ml of distilled water. Control diet is prepared with ten ml of water. The diet is divided into 3 petri dishes and 5 to 10 callow adult Ips or recently emerged adult Dendroctonus beetles are placed in each dish. Three different batches of treated diet and control diet are colonized with 10 to 20 insects. The petri dishes are incubated in the dark at 25° C., and the number of dead insects are counted 4, 7, and 10–12 days after placement on the diet. Data presented are averages from 2 or 3 distinct replicated studies for each insect species.

The results for Ips calligraphus are presented in TABLE 8, infra, and indicate that the crude mixture of compounds Ia and Ib is insecticidal.

TABLE 8

Evaluation of a mixture of compounds Ia and Ib against *Ips calligraphus*

| Treatment | Days Post Treatment | # of Insects | Average # Dead | Average % Mortality |
| --- | --- | --- | --- | --- |
| Control | 4 | 20 | 0 | 0 |
| Control | 7 | 20 | 0 | 0 |
| Control | 10 | 20 | 1 | 3 |
| Ia/Ib | 4 | 20 | 1 | 5 |
| Ia/Ib | 7 | 20 | 7 | 35 |
| Ia/Ib | 10 | 20 | 20 | 100 |

The results for the *Dendroctonus frontalis* bioassays are presented in TABLE 9, infra, and indicate that the mixture of compounds Ia and Ib is insecticidal.

TABLE 9

Evaluation of a mixture of compounds Ia and Ib against *Dendroctonus frontalis*

| Treatment | Days Post Treatment | # of Insects | Average # Dead | Average % Mortality |
| --- | --- | --- | --- | --- |
| Control | 4 | 14–20 | 0 | 0 |
| Control | 7 | 14–20 | 1 | 7 |
| Control | 10–12 | 14–20 | 3 | 16 |
| Ia/Ib | 4 | 10–20 | 1 | 5 |
| Ia/Ib | 7 | 10–20 | 1 | 5 |
| Ia/Ib | 10 | 20 | 14 | 83 |

Example 12

Activity against *Popillia japonica* (Japanese Beetle)

The crude mixture of compounds Ia and Ib is tested for pesticidal activity against third instar *Popillia japonica*. Perrenial rye grass roots (11 days old) are dipped in the crude mixture of compounds Ia and Ib (1.8 mgs of Ia and Ib per ml) and are allowed to partially dry. One third in star *Popillia japonica* larva is placed in a tin with several treated roots. After 24 hours, the roots and the larvae are covered with Wooster silt loam. Control roots are dipped in water, and untreated controls consist of larvae placed directly into the loam on day 1. The tins are incubated in the dark at 25° C., and the number of dead larvae are checked after 7, 10, 21, 28, and 36 days and control corrected mortality is reported {(Control survival—Treatment Survival)/Control Survival)×100% }. A total of 25 larvae are used for each treatment. The results, as shown in Table 10, demonstrate that the crude mixture of compounds Ia and Ib are effective against third instar *Popillia japonica*.

TABLE 10

Activity of Compounds Ia and Ib against *Popillia japonica*

| | | 7 days | 10 days | 21 days | 28 days | 36 days |
| --- | --- | --- | --- | --- | --- | --- |
| Untreated | # Dead | 2 | 2 | 4 | 5 | 5 |
| Water | # Dead | 2 | 3 | 8 | 10 | 11 |
| Control | % Control | 0 | 4.3 | 19 | 25 | 30 |
| Ia and Ib | # Dead | 6 | 8 | 13 | 14 | 15 |
| | % Control | 17.4 | 26.1 | 42.9 | 45 | 50 |

Example 13

Activity against *Epilachna varivestis* (Mexican Bean Beetle)

The crude mixture of compounds Ia and Ib (1.8 mg per ml) is tested for pesticidal activity against third instar

*Epilachna varivesis* larvae. A caged colony of *Epilachna varivesis* adults is maintained on Burpee's bush lima beans in a growth chamber under a 16:8 photoperiod at 80° F. and 50% relative humidity. Egg masses are collected and allowed to hatch in a petri dish containing a wet cotton wick and lima bean leaves. After two days, second instar larvae are collected and used for leaf dip bioassays. To perform the bioassay, bean leaves are harvested, and the petiole of a single leaf is pushed through the rubber septum of a florist's tube containing 4 ml of water. The leaves are then dipped in serial dilutions in the range of 0–12% v/v of the crude material containing compounds Ia and Ib. Once the leaves have dried, 8–10 second instar larvae are placed on each leaf. The insects, leaves, and the florist's tubes are placed in a 22 ounce paper cup, covered with fine mesh. The cups are held in the same growth chamber used fo rearing the beetle colony. Every two days the cups are removed rom the growth chamber, the larvae are censused, and the leaves are replaced with fresh treated leaves. Tests are terminated after 8 days.

The results, shown in Table 11, demonstrate the crude mixture of compounds Ia and Ib are active against *Epilachna varivesis* larvae.

TABLE 11

Dosage Mortality Response of *Epilachna varivesis* Larvae

| Days after Treatment | LC50 % | 95% Fiducial Limits | |
|---|---|---|---|
| | | lower | upper |
| 4 | 5.6 | 2.58 | 10.65 |
| 6 | 2.12 | 3.03 | 9.37 |
| 8 | 1.94 | 0.75 | 2.81 |

Example 14

Field Trial against *Leptinotarsa decemlineata* (Colorado Potato Beetle)

The trial is conducted against *Leptinotarsa decemlineata* for control in potatoes (variety Katahdin) with the crude mixture of compounds Ia and Ib applied at 50, 100, 150, and 300 grams per acre in combination with NOVODOR™ applied at 0.5 and 1.0 quart per acre, and NOVODOR™ is also applied alone at 0.5, 1.0, and 2.0 quarts per acre. The treatments are applied twice 7 days apart with a backpack $CO_2$ sprayer equipped with 3 Spray Systems TXVX-12 hollow cone nozzles per row and calibrated to deliver 32 GPA at 3 mph and 56 psi. Each treatment is replicated 4 times on plots two rows (34 inch spacing) by 25 feet in a randomized block design. *Leptinotarsa decemlineata* adults and larvae counts are made from above without disturbing the foliage over 50 feet of row/plot.

Figure 2:
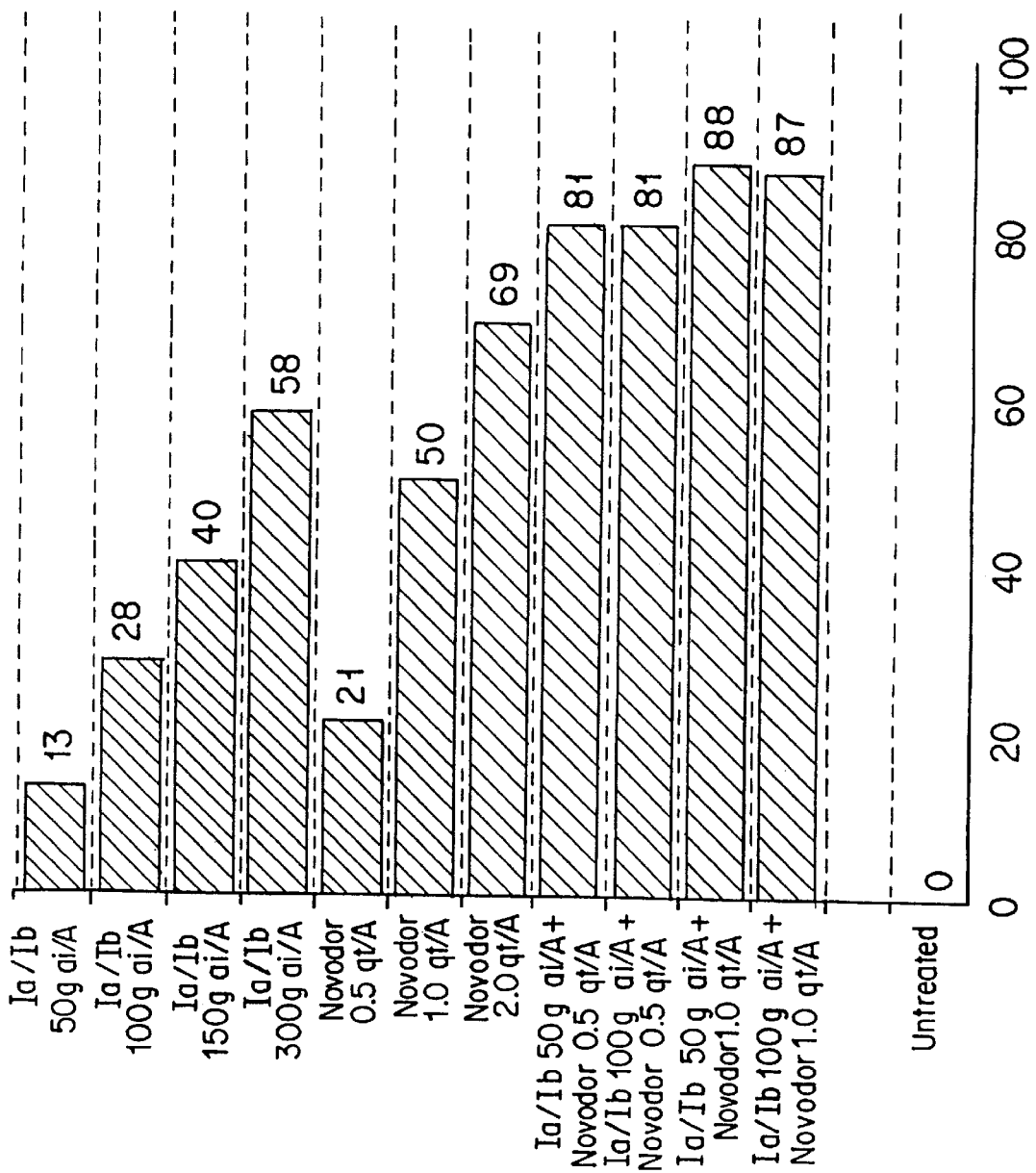
FIG. 2 shows the efficacy of Ia/Ib and NOVODOR™ synergism on *Leptitiotarsa decemlineata*.

The results, as shown in FIG. 2, demonstrate that a crude mixture of compounds Ia and Ib provide significant synergistic activity with NOVODOR™ on potatoes. At 0.5 quarts of NOVODOR™ per acre, 21% control is observed while at 50 grams of the crude mixture of compounds Ia and Ib per acre, 13% control is obtained. However, when both NOVODOR™ and the crude mixture of compounds Ia and Ib are applied together at these rates, the percent control increased to 81%. Similarly, at 100 grams of the crude mixture of compounds Ia and Ib per acre, 28% control is obtained, while at 0.5 quarts of NOVODOR™ 21% control is seen, but when both NOVODOR™ and the crude mixture of compounds Ia and Ib are applied together at these rates, the percent control increased to 81%. Furthermore, when the crude mixture of compounds Ia and Ib at 50 grams per acre and NOVODOR™ at 1.0 quart per acre are applied together, the percent control increased to 88%.

DEPOSIT OF MICROORGANISMS

The following strains of *Bacillus thuringiensis* have been deposited according to the Budapest Treaty in the Agricultural Research Service Patent Culture Collection Northern Regional Research Center (NRRL), 1815 University Street, Peoria, Ill., 61604, USA.

| Strain | Accession Number | Deposit Date |
|---|---|---|
| EMCC-0077 | NRRL B-21090 | May 10, 1993 |
| EMCC-0078 | NRRL B-21091 | May 10, 1993 |
| EMCC-0079 | NRRL B-21092 | May 10, 1993 |
| EMCC-0080 | NRRL B-21093 | May 10, 1993 |
| EMCC-0081 | NRRL B-21094 | May 10, 1993 |

The strains have been deposited under conditions that assure that access to the culture will be available during the pendency of this patent application to one determined by the Commissioner of Patents and Trademarks to be entitled thereto under 37 C.F.R. § 1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for obtaining a substantially pure substance from a strain of *Bacillus thuringiensis* which has pesticidal activity against an insect pest of the order Coleoptera and which acts with a Bacillus related pesticide against a pest, said Bacillus related pesticide selected from the group consisting of Bacillus strains, Bacillus spores, Bacillus proteins and fragments thereof, wherein said substance has the structure (I)

wherein $R_1$ is selected from the group consisting of amino, hydroxy, alkyl($C_{1-10}$), alkyl($C_{1-10}$) ester, aryl ester, halogen, $C_{1-5}$ alkoxy and amino acid;

$R_2$ is amino or alkyl ($C_{1-10}$);

$R_3$ is selected from the group consisting of hydogen, amino, hydroxy, alkyl ($C_{1-10}$), alkyl ($C_{1-10}$) ester, aryl ester, halogen, $C_{1-5}$ alkoxy, methyl amine, dimethyl amine, thionyl, methyl thionyl, cyano and salts thereof;

$R_4$ is selected from the group consisting of hydrogen, amino, hydroxy, alkyl ($C_{1-10}$), alkyl($C_{1-10}$) ester, aryl ester, halogen, $C_{1-5}$ alkoxy and salts thereof;

$R_5$ is selected from the group consisting of hydrogen, methoxy, amino, hydroxy, alkyl($C_{1-10}$), alkyl($C_{1-10}$) ester, aryl ester, halogen and $C_{1-5}$ alkoxy;

$R_6$ is selected from the group consisting of hydrogen, amino, hydroxy, alkyl($C_{1-10}$), alkyl($C_{1-10}$)ester, aryl ester, halogen and $C_{1-5}$alkoxy;

$R_7$ is selected from the group consisting of hydrogen, amino, hydroxy, alkyl($C_{1-10}$), alkyl($C_{1-10}$)ester, aryl ester, halogen, $C_{1-5}$ alkoxy and salts thereof;

$R_8$ is selected from the group consisting of hydrogen, amino, hydroxy, alkyl ($C_{1-10}$), alkyl ($C_{1-10}$) ester, aryl ester, halogen, $C_{1-5}$ alkoxy methyl amine, dimethyl amine, thionyl, methyl thionyl, cyano and salts thereof;

$R_9$ is amino or alkyl($C_{1-10}$);

$R_{10}$ is selected from the group consisting of amino, hydroxy, alkyl($C_{1-10}$), alkyl ($C_{1-10}$) ester, aryl ester, halogen, $C_{1-5}$ alkoxy and amino acid;

and $R_{11}$ and $R_{12}$ are independently selected from the group consisting of alkyl($C_{1-10}$), alkyl($C_{1-10}$)ester, aryl ester and oxygen;

wherein said aryl is selected from the group consisting of benzoyl, nitrobenzoyl, dinitrobenzoyl and halobenzoyl;

wherein said salts are selected from the group consisting of phosphate, sulfate, acetate, carbonate and nitrate; and wherein said amino acid is selected from the group consisting of alanyl, valinyl, leucinyl, isoleucinyl, phenylalanyl, glycinyl and phenylglycinyl;

comprising the steps of:

(a) culturing a *Bacillus thuringiensis* strain on a suitable growth medium;

(b) fermenting said strain to obtain a fermentation broth;

(c) separating a supernatant from said fermentation broth; and (d) obtaining a substantially pure substance from said supernatant, wherein said substance obtained from a supernatant of a fermentation of a strain of *Bacillus thuringiensis* in which essentially all of the pesticidal activity of said strain is in the supernatant of said fermentation.

2. The method according to claim 1 in which the substance has the structure wherein R, $R_1$, $R_2$, $R_3$ are hydrogen.

3. The method according to claim 1 in which the substance has the structure wherein R, $R_1$, and $R_2$ are hydrogen; and $R_3$ is hydroxy.

* * * * *

UNITED STATES PATENT AND TRADEMARK OFFICE
CERTIFICATE OF CORRECTION

Page 1 of 2

PATENT NO.: 5,976,563
DATED: November 2, 1999
INVENTOR(S) Liu et al.

It is hereby certified that error appear(s) in the above-identified patent and that said Letters Patent are hereby corrected as shown below:

On the cover page under the References Cited (under U.S. Patent Documents): 4,016,265 4/1977 Inoue et al., should be 4,916,265 Inone, et al. This was the patent number on the 1449 form.

Under "BACKGROUND OF THE INVENTION" please make the following corrections:

1. column 2, line 64, Liuthy, should be "Lüthy";

2. column 4, line 23, tewna, should be "texana";

3. column 4, line 48, phyiloplane, should be "phylloplane";

Column 5, line 40, please change the word Lepititiotarsa to Leptinotarsa;

Column 11, line 25, "*Phornia*" should be "*Phormia*";

Column 11, line 29, "*domyrrnex*" should be "*domyrme*x"

Column 11, line 30, "*Reticuliternes*" should be "*Reticulitermes*"

Column 11, line 32, "*Incisiterrnes*" should be "*Incisitermes*"

Column 11, line 58, "300C" should be "30°C";

Column 11, line 60, "*indecimpunctata*" should be "*undecimpunctata*"

UNITED STATES PATENT AND TRADEMARK OFFICE
CERTIFICATE OF CORRECTION

Page 2 of 2

PATENT NO.: 5,976,563

DATED : November 2, 1999

INVENTOR(S) Liu et al.

It is further certified that error appear(s) in the above-identified patent and that said Letters Patent are hereby corrected as shown below:

Column 15, line 42, "1 0", should be deleted;

Column 17, lines 58 and 59, "2 0" should be deleted;

Signed and Sealed this

Second Day of January, 2001

Attest:

Q. TODD DICKINSON

Attesting Officer

Commissioner of Patents and Trademarks